(12) United States Patent
Bennett et al.

(10) Patent No.: US 12,311,188 B2
(45) Date of Patent: May 27, 2025

(54) POWER IN A WEARABLE CARDIOVERTER DEFIBRILLATOR (WCD)

(71) Applicant: WEST AFFUM HOLDINGS DESIGNATED ACTIVITY COMPANY, Dublin (IE)

(72) Inventors: Brian J. Bennett, Redmond, WA (US); Kenneth F. Cowan, Everett, WA (US); Phillip D. Foshee, Jr., Woodinville, WA (US); David P. Finch, Bothell, WA (US); Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 370 days.

(21) Appl. No.: 17/732,805

(22) Filed: Apr. 29, 2022

(65) Prior Publication Data

US 2023/0089192 A1    Mar. 23, 2023

Related U.S. Application Data

(60) Provisional application No. 63/247,240, filed on Sep. 22, 2021.

(51) Int. Cl.
  *A61N 1/39* (2006.01)
  *H02J 7/34* (2006.01)
(52) U.S. Cl.
  CPC ......... *A61N 1/3925* (2013.01); *A61N 1/3904* (2017.08); *A61N 1/3981* (2013.01); *H02J 7/345* (2013.01); *H02J 2207/50* (2020.01)

(58) Field of Classification Search
  None
  See application file for complete search history.

(56) References Cited

U.S. PATENT DOCUMENTS

| | | | |
|---|---|---|---|
| 3,724,455 A | 4/1973 | Unger | |
| 4,583,524 A | 4/1986 | Hutchins | |
| 4,619,265 A | 10/1986 | Morgan et al. | |
| 4,928,690 A | 5/1990 | Heilman et al. | |

(Continued)

FOREIGN PATENT DOCUMENTS

WO    9839061 A2    9/1998

OTHER PUBLICATIONS

Heartstart MRx and XL AED Algorithm—Application Note, Jul. 2001, Edition 2 Philips Healthcare, USA.

(Continued)

*Primary Examiner* — Mallika D Fairchild
(74) *Attorney, Agent, or Firm* — Polsinelli PC

(57) ABSTRACT

A wearable medical device comprising monitoring circuitry to monitor one or more patient parameters of a patient and defibrillation circuitry to provide one or more defibrillation shocks to the patient responsive to a control signal from the monitoring circuitry. The defibrillation circuitry comprises a defibrillation capacitor to provide energy for the one or more defibrillation shocks. The wearable medical device also comprises a power source to provide power to the monitoring circuitry and the defibrillation circuitry. The power source comprises a low current power source (LCPS) to provide power to the monitoring circuitry, and a high current power source (HCPS) to provide power to the defibrillation circuitry.

19 Claims, 7 Drawing Sheets

(56) References Cited

U.S. PATENT DOCUMENTS

| | | | |
|---|---|---|---|
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,662,690 A | 9/1997 | Cole et al. | |
| 5,773,961 A * | 6/1998 | Cameron | H01M 10/48 320/132 |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,024,037 B2 | 9/2011 | Kumar | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,838,235 B2 | 9/2014 | Cowan et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 2002/0169584 A1 | 11/2002 | Fu et al. | |
| 2003/0080712 A1 * | 5/2003 | Tamura | A61N 1/3975 320/103 |
| 2003/0158593 A1 | 8/2003 | Heilman et al. | |
| 2003/0181950 A1 * | 9/2003 | Powers | A61N 1/3975 607/5 |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson et al. | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0150008 A1 | 1/2012 | Lanar et al. | |
| 2012/0112903 A1 | 5/2012 | Kaib et al. | |
| 2012/0144551 A1 | 6/2012 | Guldalian | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0307685 A1 | 11/2013 | Sholder | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0043149 A1 | 2/2014 | Cowan et al. | |
| 2014/0070957 A1 | 3/2014 | Longinotti-Buitoni et al. | |
| 2014/0142445 A1 | 5/2014 | Banet et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0119725 A1 | 4/2015 | Martin et al. | |
| 2015/0328472 A1 | 11/2015 | Sullivan et al. | |
| 2016/0004831 A1 | 1/2016 | Carlson et al. | |
| 2016/0066801 A1 | 3/2016 | Kahlert et al. | |
| 2016/0067514 A1 | 3/2016 | Sullivan | |
| 2016/0082277 A1 | 3/2016 | Foshee, Jr. et al. | |
| 2016/0135706 A1 | 5/2016 | Sullivan et al. | |
| 2016/0287470 A1 | 10/2016 | Lewis et al. | |
| 2016/0331986 A1 * | 11/2016 | Piha | G08B 21/0453 |
| 2017/0014079 A1 | 1/2017 | Lee et al. | |
| 2017/0056682 A1 * | 3/2017 | Kumar | A61N 1/3968 |
| 2018/0049649 A1 | 2/2018 | Addison et al. | |
| 2018/0199834 A1 | 7/2018 | Siedenburg | |
| 2018/0243578 A1 * | 8/2018 | Volosin | A61N 1/3987 |
| 2018/0333058 A1 | 11/2018 | Coulon et al. | |
| 2019/0014997 A9 | 1/2019 | Siedenburg | |
| 2019/0030351 A1 | 1/2019 | Sullivan et al. | |
| 2019/0030352 A1 | 1/2019 | Sullivan et al. | |
| 2019/0168011 A1 | 6/2019 | Medema | |
| 2020/0121938 A1 | 4/2020 | Piha et al. | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

POWER IN A WEARABLE CARDIOVERTER DEFIBRILLATOR (WCD)

CROSS-REFERENCE TO RELATED APPLICATIONS

The present application claims the benefit of U.S. Provisional Application No. 63/247,240 filed Sep. 22, 2021. Said Application No. 63/247,240 is hereby incorporated herein by reference in its entirety.

BACKGROUND

Wearable cardioverter defibrillators (WCDs) analyze patient signals to determine if the patient is experiencing a cardiac arrest. If a ventricular tachycardia/ventricular fibrillation (VT/VF) arrest is suspected, the WCD will alarm to warn the patient and bystanders of an impending shock, and if no stop signal is received then the WCD will apply one or more therapeutic shocks to the patient.

Monitoring components of a wearable defibrillator can include, for example, circuitry for electrocardiogram (ECG) measuring, a controller or processor to analyze ECG signals and decide whether defibrillation is necessary, and the various other support circuits. The power draw for these monitoring components of the wearable defibrillator can be sufficiently low such that a battery optimized for small size and high capacity at low output currents could have a series resistance that is too high to support charging the defibrillation capacitor of the wearable defibrillator. Existing solutions use an overdesigned battery to support the defibrillator capacitor charger in addition to providing power to the other low-power circuitry.

DESCRIPTION OF THE DRAWING FIGURES

Claimed subject matter is particularly pointed out and distinctly claimed in the concluding portion of the specification. However, such subject matter can be understood by reference to the following detailed description when read with the accompanying drawings in which:

Figure 1:
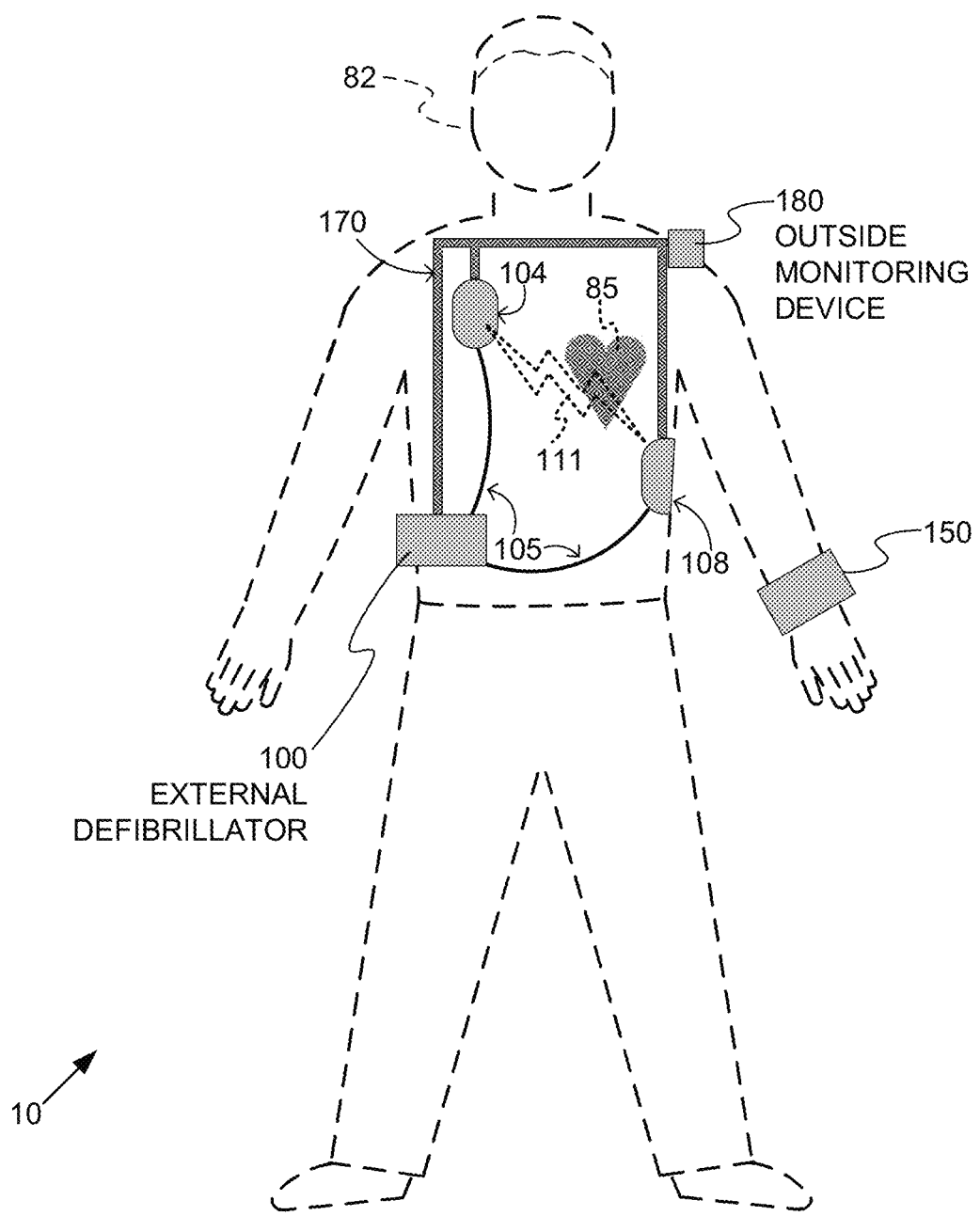
FIG. 1 is a diagram of a WCD system including an external defibrillator in accordance with one or more embodiments.

It will be appreciated that for simplicity and/or clarity of illustration, elements illustrated in the figures have not necessarily been drawn to scale. For example, the dimensions of some of the elements can be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter can be practiced without these specific details. In other instances, well-known methods, procedures, components and/or circuits have not been described in detail.

In the following description and/or claims, the terms coupled and/or connected, along with their derivatives, can be used. In particular embodiments, connected can be used to indicate that two or more elements are in direct physical and/or electrical contact with each other. Coupled can mean that two or more elements are in direct physical and/or electrical contact. Coupled, however, can also mean that two or more elements can not be in direct contact with each other, but yet can still cooperate and/or interact with each other. For example, "coupled" can mean that two or more elements do not contact each other but are indirectly joined together via another element or intermediate elements. Finally, the terms "on," "overlying," and "over" can be used in the following description and claims. "On," "overlying," and "over" can be used to indicate that two or more elements are in direct physical contact with each other. It should be noted, however, that "over" can also mean that two or more elements are not in direct contact with each other. For example, "over" can mean that one element is above another element but not contact each other and can have another element or elements in between the two elements. Furthermore, the term "and/or" can mean "and", it can mean "or", it can mean "exclusive-or", it can mean "one", it can mean "some, but not all", it can mean "neither", and/or it can mean "both", although the scope of claimed subject matter is not limited in this respect. In the following description and/or claims, the terms "comprise" and "include," along with their derivatives, can be used and are intended as synonyms for each other.

Referring now to FIG. 1, a diagram of a WCD system including an external defibrillator in accordance with one or more embodiments will be discussed. The WCD system 10 of FIG. 1 can be worn by a patient 82 to detect heart arrhythmias in the patient 82 and to apply one or more therapeutic shocks to the patient 82. Patient 82 can also be referred to as a person and/or wearer since the patient is wearing components of the WCD system 10. Patient 82 can be ambulatory, which means that patient 82 can walk around while wearing the wearable portion of the WCD system 10, and the patient 82 is not necessarily bed ridden. It should be noted that the wearer can also wear the WCD system 10 if the wearer is bed ridden or sleeping. While patient 82 can be considered to be a user of the WCD system 10, there can be users of the WCD system 10 other than the patient 82. For example, a user of the wearable cardioverter defibrillator (WCD) system 10 can also be a clinician such as a doctor, nurse, emergency medical technician (EMT), or other similarly tasked individual or group of individuals. In some cases, a user can be a bystander. The particular context of these and other related terms within this description should be interpreted accordingly.

A WCD system 10 according to embodiments herein can be configured to defibrillate the patient 82 who is wearing the designated parts of the WCD system 10. Defibrillating can be done by the WCD system 10 by delivering an electrical charge to the patient's body in the form of an electric shock. The electric shock can be delivered in one or more pulses.

FIG. 1 shows an example WCD system 10 with a sample external defibrillator 100. In the context of a WCD system 10, defibrillator 100 can also be referred to as a main electronics module that includes an energy storage module within a housing of the defibrillator 100. The energy storage module can be configured to store an electrical charge. Other components can cause at least some of the stored electrical charge to be discharged via electrodes through the patient 82 to deliver one or more defibrillation shocks through the patient 82. As described in more detail with respect to FIG. 2 and FIG. 3 below, the housing of defibrillator 100 can accommodate a power source which can include a low current power source (LCPS) and a high current power source (HCPS), and an energy storage module that can include a high voltage (HV) capacitor or defibrillation capacitor and/or an HV capacitor charger to charge the defibrillation capacitor.

As will be discussed further herein, the electronic module 100 can further include a supercapacitor to operate as the high current power source. The supercapacitor can be configured to provide at least some power to the processor of the electronic module in some embodiments, for example when the low current power source is depleted and some charge remains in the supercapacitor, although the scope of the disclosed subject matter is not limited in this respect. In some examples, the energy provided by the supercapacitor can facilitate performance of housekeeping tasks such as powering off, closing log files and/or data acquisition files, and/or placing the high voltage therapy circuits into a safe state. Such a supercapacitor (SC) can comprise or be referred to as an Electrochemical Double Layer Capacitor (EDLC), a supercap, or ultracapacitor, and can comprise a high-capacity capacitor with capacitance values higher than other conventional capacitors. Although a supercapacitor is discussed herein for purposes of example, the high current power source (HCPS) is not limited to a supercapacitor wherein other suitable devices can be deployed as the HCPS, and the scope of the disclosed subject matter is not limited in this respect.

FIG. 1 also shows sample defibrillation electrodes 104 and 108 which are coupled to external defibrillator 100 via electrode leads 105. Defibrillation electrodes 104 and 108 can be configured to be worn by patient 82 in a number of ways. For instance, defibrillator 100 and defibrillation electrodes 104 and 108 can be coupled to support structure 170, directly or indirectly. In other words, support structure 170 can be configured to be worn by ambulatory patient 82 to maintain at least one of electrodes 104 or 108 on the body of ambulatory patient 82 while patient 82 is moving around or performing other activity. The electrode can be thus maintained on the body by being attached to the skin of patient 82, simply pressed against the skin directly or through garments, fabric, and so on. In some embodiments the electrode is not necessarily pressed against the skin but becomes biased that way upon sensing a condition that could merit intervention by the WCD system 10. In addition, many of the components of defibrillator 100 can be considered coupled to support structure 170 directly, or indirectly via at least one of defibrillation electrodes 104 or 108.

When defibrillation electrodes 104 and 108 make good electrical contact with the body of patient 82, defibrillator 100 can administer, via electrodes 104 and 108, a brief, strong electric pulse 111 through the body. Pulse 111 can be referred to as a shock, defibrillation shock, therapy, electrotherapy, therapy shock, and so on. Pulse 111 is intended to go through and restart the patient's heart 85 in an effort to save the life of patient 82. Pulse 111 can further include one or more pacing pulses of lesser magnitude to simply pace heart 85 if needed, and so on.

A defibrillator generally can determine whether to defibrillate or not based on an electrocardiogram (ECG) signal of the patient 82. External defibrillator 100, however, can initiate defibrillation or hold-off defibrillation based on a variety of inputs, with the ECG signal merely being one of these inputs.

A WCD system 10 according to embodiments can obtain data from patient 82. For collecting such data, the WCD system 10 can optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, a parameter of the WCD system 10, or a parameter of the environment as will be described further herein.

For some of these parameters, device 180 can include one or more sensors or transducers. Each one of such sensors can be configured to sense a parameter of patient 82 and to render an input responsive to the sensed parameter. In some embodiments, the input can be quantitative such as values of a sensed parameter. In other embodiments, the input can be qualitative such as informing whether or not a threshold is crossed, and so on. Sometimes these inputs about patient 82 are also referred to herein as physiological inputs and patient inputs. In some embodiments, a sensor can be construed more broadly, as encompassing many individual sensors.

FIG. 1 also depicts other components of a WCD system made according to embodiments. One such component is a support structure 170 that is wearable by ambulatory patient 82. Accordingly, support structure 170 can be configured to be worn by ambulatory patient 82 for at least several hours per day, and for at least several days, even a few months. It will be understood that support structure 170 is shown only generically in FIG. 1, and partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, and so on. In such embodiments, such items can be worn similarly to analogous articles of clothing. In embodiments, support structure 170 could include a harness, one or more belts or straps, etc. In such embodiments, such items can be worn by the patient around the torso, hips, over the shoulder, and so on. In some embodiments, support structure 170 can include a container or housing which optionally can be waterproof. In such embodiments, the support structure can be worn by being attached to the patient's body by adhesive material, for example as shown and described in issued U.S. Pat. No. 8,024,037 B2 which is incorporated herein by reference in its entirety. Support structure 170 can also be implemented as described for the support structure of published application Pub. No. US 2017/0056682 A1 which is incorporated herein by reference in its entirety. In such embodiments, additional components of the WCD system 10 can be in the housing of a support structure 170 instead of being attached externally to the support structure 170, for example as described in Pub. No. US 2017/0056682 A1. Furthermore, there can be other examples, and the scope of the disclosed subject matter is not limited in these respects.

Optionally, device 180 is physically coupled to support structure 170. In addition, device 180 can be communicatively coupled with other components that are coupled to support structure 170. Such communication can be implemented by a communication module, as will be deemed applicable by a person skilled in the art in view of this description.

In some embodiments, one or more of the components of the shown WCD system 10 can be customized for patient 82. This customization can include a number of aspects. For example, support structure 170 can be fitted to the body of patient 82. For another example, baseline physiological parameters of patient 82 can be measured, such as the heart rate of patient 82 while resting, while walking, motion detector outputs while walking, etc. The measured values of such baseline physiological parameters can be used to customize the WCD system 10 in order to make its diagnoses more accurate since the bodies of different patients can differ from one another. Such parameter values can be stored in a memory or storage device of the WCD system 10. Moreover, a programming interface can be made according to some embodiments which receives such measured values of baseline physiological parameters. Such a programming interface can automatically input these parameters along with other data in the WCD system 10.

In some embodiments, WCD system 10 can include one or more additional external devices 150 that can be worn by the patient 82, for example on a wrist or ankle, to provide additional patient parameters to the external defibrillators 100, and/or to provide a user interface to be used to control the WCD system 10. Such external devices 150 can include, for example, an additional heart rate monitor, a non-invasive blood pressure monitor or cuff, a pulse oximeter device to monitor saturation of peripheral oxygen (SpO2), a respiration monitor, or a watch with a graphical user interface, and so on, and the scope of the disclosed subject matter is not limited in these respects.

Figure 2:
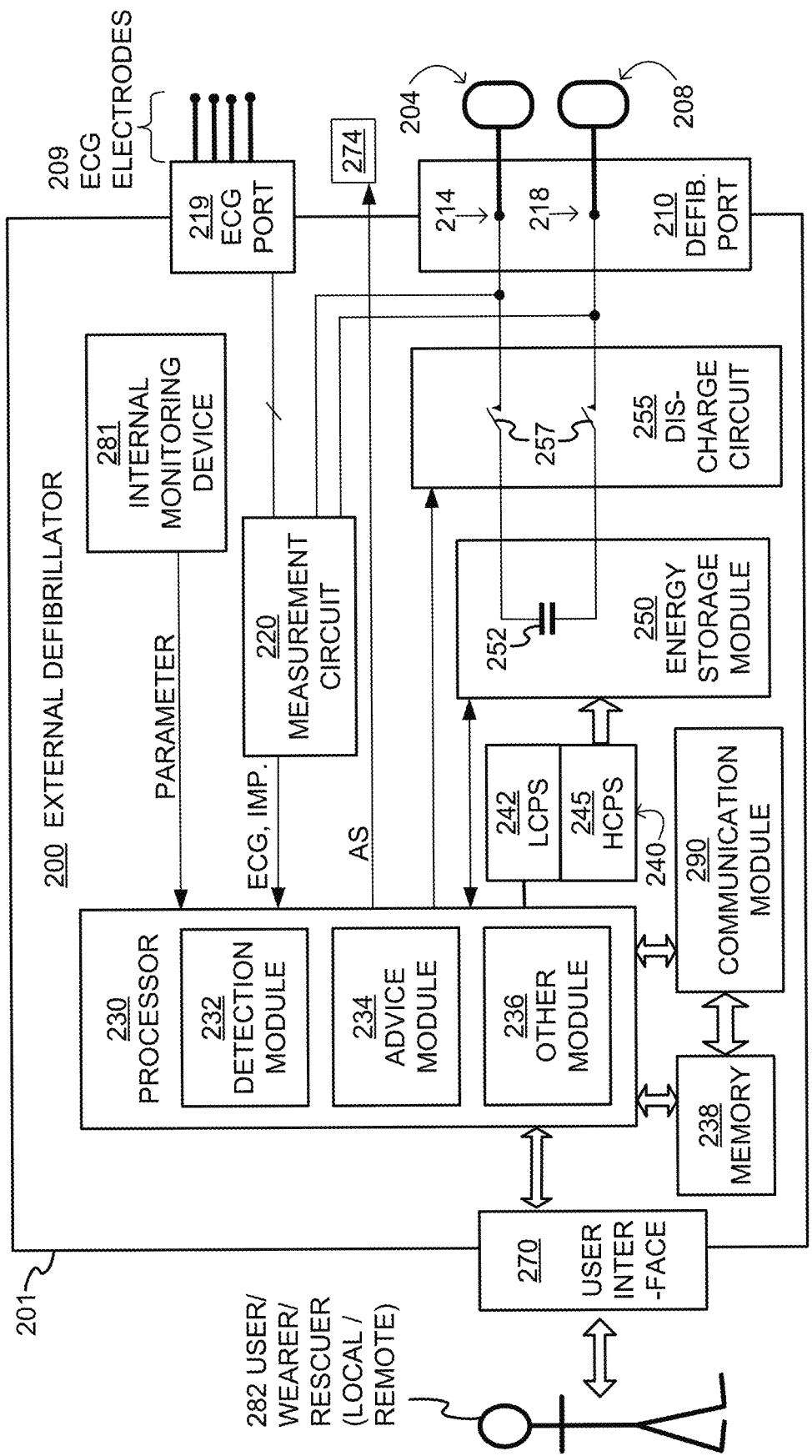
FIG. 2 is a diagram of components of an external defibrillator in accordance with one or more embodiments.

Referring now to FIG. 2, a diagram of components of an external defibrillator in accordance with one or more embodiments will be discussed. The components of external defibrillator 200 can be included in external defibrillator 100 of FIG. 1. Although FIG. 2 shows various components of defibrillator, defibrillator 200 can optionally include other components not shown in FIG. 2, or fewer components, in various alternate arrangements and configurations of the components, and the scope of the disclosed subject matter is not limited in this respect. The components shown in FIG. 2 can be provided in a housing 201 which can also be referred to as casing 201. FIG. 2 illustrates a method of power sourcing and distribution in a defibrillator 200 such as utilized in a wearable cardioverter defibrillator (WCD) system 10. The power source 240 comprises a low current power source (LCPS) 242 configured to power monitoring aspects of defibrillator 200 and which can be separate from a high current power source (HCPS) 245 configured to power the therapy aspects of the defibrillator 200. The power source 240 in FIG. 2 can include the low current power source (LCPS) 240 and the high current power source (HCPS) 245 among other devices or circuits. The HCPS 245 can be configured to power the energy storage module 250 comprising a high voltage capacitor or defibrillation capacitor 252 and/or a capacitor charger. In some embodiments, the HCPS 245 can include a supercapacitor.

External defibrillator 200 is intended for a patient who would be wearing it, such as ambulatory patient 82 of FIG. 1. Defibrillator 200 can further include a user interface 270 for a user 282. User 282 can be patient 82, also known as wearer 82. User 282 can be a local rescuer at the scene such as a bystander who might provide assistance or a trained person. User 282 might be a remotely located trained caregiver in interfacing with the WCD system 10.

User interface 270 can be implemented in a number of ways. User interface 270 can include output devices which can be visual, audible, or tactile, for communicating to a user by outputting images, sounds, or vibrations. Images, sounds, vibrations, or anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds, and/or words to warn bystanders, and so on.

User interface 270 can further include input devices for receiving inputs from users. Such input devices can include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 can include an internal monitoring device 281. Device 281 is called an "internal" device because it is incorporated within housing 201. Monitoring device 281 can sense or monitor patient parameters such as patient physiological parameters, system parameters and/or environmental parameters, motion parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 and/or 180 can include one or more sensors.

Defibrillator 200 can perform processing of monitoring and therapy functions and storing of data in non-volatile memory. The data can also be transmitted by the communication module over a wireless connection to a location accessible from the internet.

Processing data, data storage, and data transmission involves power. A patient can be wearing the WCD system for an extended time, for example up to 90 days or longer. A rechargeable battery can be used to power the WCD system. When a rechargeable battery needs to be charged during the wear time, the defibrillator 200 is configured to use a supercapacitor to power the processor and control circuitry. Such a situation can occur, for example, when the charge in the battery is depleted or otherwise below a threshold level during wear so that the processor and control circuit can be powered by the supercapacitor for a period of time. The supercapacitor also can power the WCD system while the rechargeable battery is being recharged. In one example, defibrillator 200 includes a battery, such as a standard lithium-ion battery, supplying a voltage range of about 3.3V to 4.2V. The processor can be powered by a voltage regulator connected to the battery. The power draw can be 1 W and the current draw can be 250 mA. In some examples, a supercapacitor rated at 470 mF and 5.4 V can be connected across the output of the regulator.

In one embodiment, when the battery is recharging and/or the regulator loses power source, the example supercapacitor connected across the output of the regulator can begin to discharge. At 250 mA, the dV/dt is 0.53 V/s giving the processor approximately one second to perform the housekeeping duties required to shut down cleanly and safely. In a further embodiment, a sensing circuit can detect when the battery is removed or enters a charging phase, so that a shutdown processes can be triggered. In one example, a comparator circuit connected to the battery input with a threshold can be set below the voltage needed to power the voltage regulator.

Patient parameters can include patient physiological parameters. Patient physiological parameters can include, for example and without limitation, those physiological parameters that can be of any help in detecting, by the WCD system 10, whether or not the patient is in need of a shock or other intervention or assistance. Patient physiological parameters can also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds, or pulse. Accordingly, monitoring devices 180 and 281 can include one or more sensors configured to acquire patient physiological signals. Examples of such sensors or transducers include one or more electrodes to detect ECG data, a perfusion sensor, a pulse oximeter, a device for detecting blood flow, for example a Doppler device, a sensor for detecting blood pressure, for example a cuff, an optical sensor, illumination detectors and sensors working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, or pulse rate sensors. In addition, a person skilled in the art can implement other ways of performing pulse detection, and the scope of the disclosed subject matter is not limited in these respects.

In some embodiments, the local parameter can be a trend that can be detected in a monitored physiological parameter of patient 282. A trend can be detected by comparing values of parameters at different times over short and long terms. Parameters whose detected trends can particularly help a cardiac rehabilitation program include: a) cardiac function, for example ejection fraction, stroke volume, cardiac output, and so on; b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, and so on; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus can be also what they said, and so on, plus optionally the history of these parameters. Alternatively, one of these monitoring devices can include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. In some examples, one or more accelerometers can be used for motion detection. Patient state parameters can be very helpful in narrowing down the determination of whether sudden cardiac arrest (SCA) is indeed taking place.

System parameters of a WCD system 10 can include system identification, battery status, system date and time, reports of self-testing, records of data entered, records of episodes and intervention, and so on. In response to the detected motion event, the motion detector can render or generate, from the detected motion event or motion, a motion detection input that can be received by a subsequent device or functionality.

Environmental parameters can include ambient temperature, humidity, and pressure. In some examples, one or more environmental parameters can be determined based least in part on one or more other environmental parameters. For example, relative humidity or a "feels like" temperature can be determined based at least in part on temperature and humidity. In such examples, 100 degrees Fahrenheit in high humidity can be unbearable and put more strain on the patient, while 100 degrees Fahrenheit in low humidity could be tolerable to the patient. Moreover, a humidity sensor can provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214 and 218. Leads of defibrillation electrodes 204 and 208, such as leads 105 of FIG. 1, can be plugged into defibrillation port 210 to make electrical contact with nodes 214 and 218, respectively. It is also possible that defibrillation electrodes 204 and 208 are connected continuously to defibrillation port 210, instead. Either way, defibrillation port 210 can be used for guiding, via electrodes, to the wearer at least some of the electrical charge that has been stored in an energy storage module 250 that is described more fully later herein. The electric charge will be the shock for defibrillation, pacing, and so on.

Defibrillator 200 can optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, for example a 12-lead signal, or a signal from a different number of leads, especially if they make good electrical contact with the body of the patient and in particular with the skin of the patient. As with defibrillation electrodes 204 and 208, the support structure 170 can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204 and 208.

Optionally, a WCD system 10 according to some embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid can be in the form of a low-viscosity gel so that it does not flow away, after being deployed, from the location it is released near the electrode. The fluid can be used for both defibrillation electrodes 204 and 208, and for sensing electrodes 209. The fluid can be initially stored in a fluid reservoir, not shown in FIG. 2. Such a fluid reservoir can be coupled to the support structure. In addition, a WCD system 10 according to some embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal (AS) from a processor 230, which is described more fully herein.

In some embodiments, defibrillator 200 also includes a measurement circuit 220. Measurement circuit 220 senses one or more electrical physiological signals of the patient from sensor port 219, if provided. Even if defibrillator 200 lacks sensor port 219, measurement circuit 220 can optionally obtain physiological signals through nodes 214 and 218 instead when defibrillation electrodes 204 and 208 are attached to the patient. In these cases, the input reflects an ECG measurement. The patient parameter can be an ECG which can be sensed as a voltage difference between electrodes 204 and 208. In addition, the patient parameter can be an impedance which can be sensed between electrodes 204, 208 and/or between the connections of sensor port 219 considered pairwise. Sensing the impedance can be useful for detecting, among other things, whether these electrodes 204 and 208 and/or sensing electrodes 209 are not making good electrical contact with the patient's body. These patient physiological signals can be sensed when available. Measurement circuit 220 can then render or generate information about them as inputs, data, other signals, and so on. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. The information rendered by measurement circuit 220 is output from it. This information can be called an input because it is received as an input by a subsequent device or functionality.

Defibrillator 200 also includes a processor 230. Processor 230 can be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can include, or have access to, a non-transitory storage medium, such as memory 238 that is described more fully later in this document. Such a memory can have a non-volatile component for storage of machine-readable and machine-executable instructions. A set of such instructions can also be called a program. The instructions, which can also be referred to as software, generally provide functionality by performing acts, operations and/or methods as can be disclosed herein or understood by one skilled in the art in view of the disclosed embodiments. In some embodiments, and as a matter of convention used herein, instances of the software can be referred to as a module and by other similar terms. Generally, a module includes a set of the instructions so as to offer or fulfill a particular functionality. Embodiments of modules and the functionality delivered are not limited by the embodiments described herein.

Defibrillator 200 can also include a memory 238 which can work together with processor 230. Memory 238 can be implemented in a number of ways. Such ways include, by way of example and not of limitation, volatile memories, nonvolatile memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230 which processor 230 can read and execute. More particularly, the programs can include sets of instructions in the form of code which processor 230 can be able to execute upon reading. The programs can also include other information such as configuration data, profiles, scheduling etc. that can be acted on by the instructions. Executing is performed by physical manipulations of physical quantities, and can result in functions, operations, processes, acts, actions and/or methods to be performed, and/or the processor to cause other devices or components or blocks to perform such functions, operations, processes, acts, actions and/or methods. The programs can be operational for the inherent needs of processor 230 and can also include protocols and ways that decisions can be made by advice module 234. In addition, memory 238 can store prompts for user 282 if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200 or be stored there after it is received by defibrillator 200.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, can be used by the VF detector to determine whether the patient is experiencing VF. Detecting VF is useful because VF typically results in SCA. Detection module 232 can also include a Ventricular Tachycardia (VT) detector, and so on.

Another such module in processor 230 can be an advice module 234 which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal can be corrupted by electrical noise which makes it difficult to analyze. Too much noise sometimes causes an incorrect detection of a heart arrhythmia, resulting in a false alarm to the patient. Noisy ECG signals can be handled as described in published patent application Pub. No. US 2019/0030351 A1, and also in published application Pub. No. US 2019/0030352 A1, both by the same applicant and both incorporated herein by reference in their entireties. Processor 230 can include additional modules, such as other module 236, for other functions. In addition, if internal monitoring device 281 is indeed provided, processor 230 can receive its inputs, and so on.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data can be patient data, event information, therapy attempted, cardiopulmonary resuscitation (CPR) performance, system data, environmental data, and so on. For example, communication module 290 can transmit wirelessly, for example on a daily basis, heart rate, respiratory rate, or other vital signs data to a server accessible over the internet, for instance as described in Pub. No. US 2014/0043149 A1 which is hereby incorporated herein by reference in its entirety. This data can be analyzed directly by the patient's physician and can also be analyzed automatically by algorithms designed to detect a developing illness and then notify medical personnel via text, email, phone, and so on. Module 290 can also include such interconnected sub-components as can be deemed necessary by a person skilled in the art, for example an antenna, portions of a processor, supporting electronics, outlet for a telephone or a network cable, and so on.

Defibrillator 200 can also include a power supply 240 including a low current power source (LCPS) 242 and a high current power source (HCPS) 245. To enable portability of defibrillator 200, power supply 240 including LCPS 242 or HCPS 245 can include a battery. Such a battery can be rechargeable. Sometimes a combination can comprise rechargeable and non-rechargeable batteries. Other embodiments of power sources 242 and 245 can include an alternating current (AC) power override when external AC power is available, an energy-storing capacitor, and so on. Appropriate components can be included to provide for charging or replacing power source 242 and/or 245. In some embodiments, power source 242 or 245 is controlled and/or monitored by processor 230. In one embodiment the LCPS 242 can power monitoring circuitry, including the processor 230, ECG measurement circuit 220, communication module 290, memory 238, or user interface 270, and a HCPS 245 is dedicated to charge the energy storage module's 250, defibrillation capacitor 252, or power a high current-draw circuit such as a squib firing circuit or fluid deployment mechanism, as further described in more detail below.

Defibrillator 200 can additionally include an energy storage module 250. Energy storage module 250 can be coupled to the support structure of the WCD system 10, for example either directly or via the electrodes and their leads. Module 250 is where some electrical energy can be stored temporarily in the form of an electrical charge when preparing it for discharge to administer a shock. In some embodiments, module 250 can be charged from HCPS 245 to the desired amount of energy, as controlled by processor 230. In typical implementations, module 250 includes a defibrillation capacitor 252 which can be a single capacitor or a system of capacitors, and so on. In some embodiments, energy storage module 250 includes a device that exhibits high power density. As described above, capacitor 252 can store the energy in the form of an electrical charge for delivery to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 includes a discharge circuit 255. When the decision is to shock, processor 230 can be configured to control discharge circuit 255 to discharge through the patient at least some of all of the electrical charge stored in energy storage module 250. Discharging can be to nodes 214 and 218, and from there to defibrillation electrodes 204 and 208, so as to cause a shock to be delivered to the patient. Circuit 255 can include one or more switches 257. Switches 257 can be made in a number of ways, such as by an H-bridge circuit, and so on. Circuit 255 could also be thus controlled via processor 230, and/or user interface 270.

A time waveform of the discharge can be controlled by thus controlling discharge circuit 255. The amount of energy of the discharge can be controlled by how much energy storage module has been charged, and also by how long discharge circuit 255 is controlled to remain open.

Figure 3:
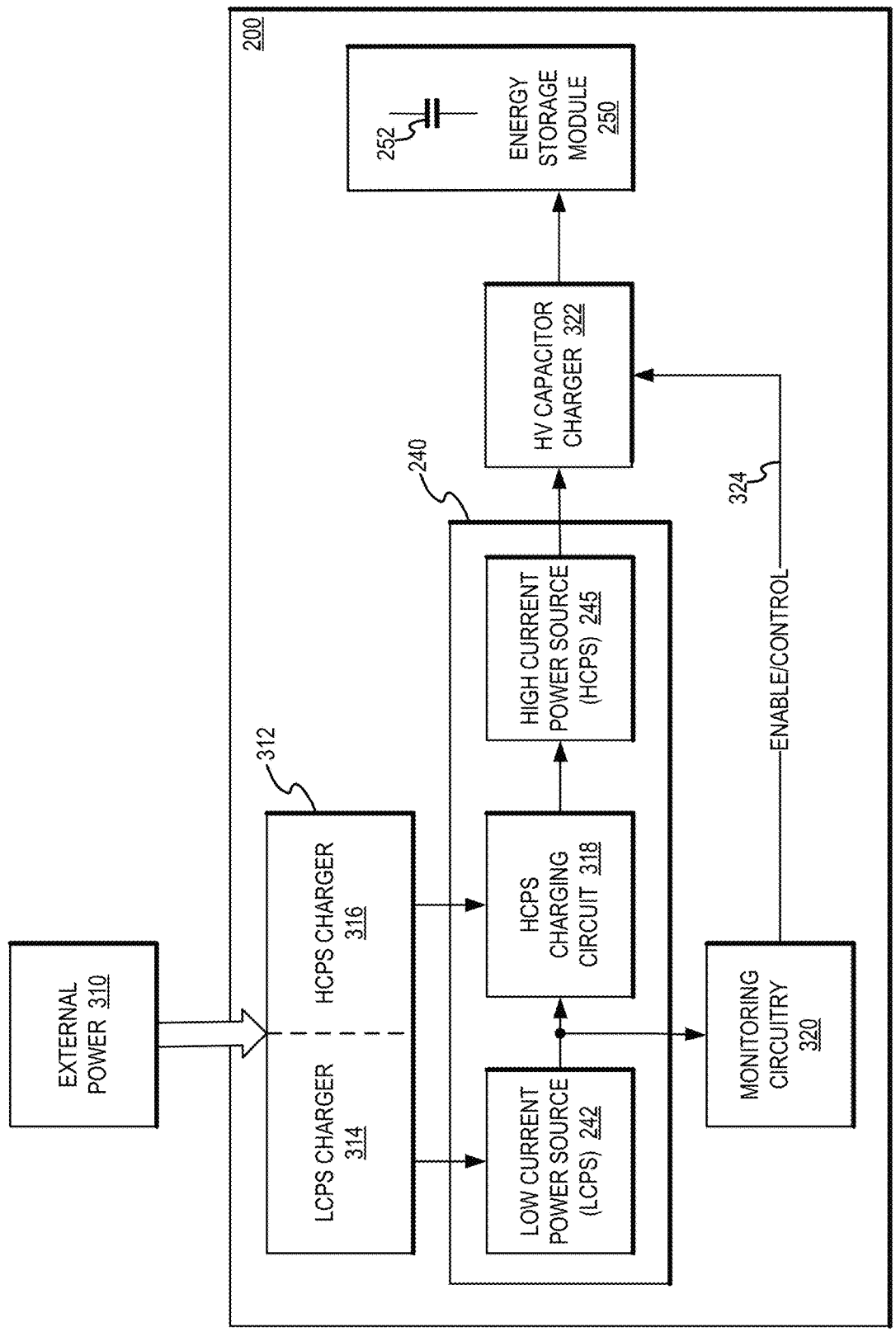
FIG. 3 is a diagram of power components of a WCD system in accordance with one or more embodiments.

Referring now to FIG. 3, a diagram of power components of a WCD system in accordance with one or more embodiments will be discussed. In an example embodiment, a WCD system 10 can include an external defibrillator 200 that operates from a low current power source (LCPS) 242 and a high current power source (HCPS) 245 as described herein above with respect to FIG. 2. An external power source 310 can provide power to the defibrillator 200. The external power source 310 can comprise an alternating current (AC) input or a direct current (DC) input to the defibrillator 200. The external power source 310 can provide power to a charging circuit 312 that can include a LCPS charger 314 to charge LCPS 242 and an HCPS charger 316 to charge HCPS 245, optionally via HCPS charging circuit 318. In some embodiments, the charging circuit 312 can be located in the external power source 310 for example in an external power adapter. After the LCPS 242 and/or the HCPS 245 are charged, the defibrillator 200 can be disconnected from external power source 310 to allow the patient 82 or 282 to be free to wear WCD system 10 untethered from external power source 310. In some examples, power supply 240 may be disposed in a self-contained, removable module. In such embodiments, the user can have at least two such power modules 240 wherein a fully charged power supply module 240 can be inserted into the defibrillator 200 to power the defibrillator while the other power supply module 240 is being charged by an external charger. In such an arrangement, the defibrillator 200 does not need to be charged while in use, and patient does not need to be tethered to a charger.

In some embodiments, the LCPS 242 can be used to power the monitoring circuitry 320 while the separate HCPS 245 can power or charge the therapy circuitry of the defibrillator 200. Such an arrangement is in contrast to systems that use a single power source or battery to provide power both for monitoring and for providing therapy. The overall size of the power supply 240 comprising a LCPS 242 and HCPS 245 can be smaller in size and weight and/or faster at charging the defibrillation capacitor 252 of the energy storage module 250, and/or more efficient, when compared to a single power source or a single battery driven system. During portable or ambulatory deployment of defibrillator 200, the LCPS 242 can provide operational power to monitoring circuitry 320 of WCD system 10. When monitoring circuitry 320 detects and/or confirms that the patient is experiencing a shockable event, the monitoring circuitry 320 can provide an enable or control signal 324 to the high voltage (HV) capacitor charger 322 to cause HCPS 245 to charge the defibrillation capacitor 252 in order to provide one or more shocks 111 to the patient 82 or 282. In some embodiments, after the energy storage module 250 provides one or more shocks 111 and the defibrillation capacitor 252 is discharged, the LCPS 242 can recharge the HCPS 245 so that the HCPS 245 can then be used to recharge defibrillation capacitor 252 so that one or more additional shocks 111 can be delivered to the patient. This discharge and recharge process can undergo one or more iterations until the patient is no longer experiencing a shockable event, or at least until all of the energy in LCPS 242, HCPS 245, and/or defibrillation capacitor 252 are sufficiently depleted below a level at which additional recharges or shocks can be provided.

In the embodiment shown in FIG. 3, the LCPS 242 and the HCPS 245 can be charged independently from each other. In one embodiment, the HCPS charger 316 charging the HCPS 245 can be different from the LCPS 314 charging the LCPS 242. In this example, the LCPS 242 is not the primary source of charging HCPS 245. In a further embodiment, the source charging the HCPS 245 and the source charging the LCPS 242 can be included in one charging module 312, either external to defibrillator 200 at least in part or internal to defibrillator 200 at least in part. In another embodiment, the source HCPS charger 316 and the LCPS charger 314 can comprise different, separate modules. In any of such embodiments, the power supply 240 can be contained in a removable module that can be removed from the defibrillator 200 and can be charged by an external charger a discussed herein above. In some examples, LCPS charger 314 can comprise a USB or USB-C charger or similar standard charging device.

The LCPS 242 can provide power to the monitoring controller/circuitry 320. In a further embodiment, the LCPS 242 can be configured to also charge HCPS 245, for example via HCPS charging circuit 318. In some embodiments, LCPS 242 can be used to top off or otherwise provide a maintenance charge to HCPS 245 for example to account for charge leakage and/or self-discharge in the HCPS 245. In other examples, LCPS 242 can be used to recharge HCPS 245 after HCPS 245 is used to charge defibrillation capacitor 252 when therapy is provided to the patient 82 or 282. The monitoring controller circuitry 320 including the processor 230 can be configured to enable the HV capacitor charger 322 to cause power to be supplied by the HCPS 245 to the defibrillation capacitor 252. Following defibrillation shocks, the LCPS 242 can recharge the HCPS 245 to enable further shocks prior to the availability of independent, external charging from external power source 310. The recharge time can be a function of the overall rated values of the HCPS 245, for example capacitance, charging current, and the LCPS 242 available capacity less any energy or current for operating monitoring circuitry of defibrillator 200.

Figure 4A:
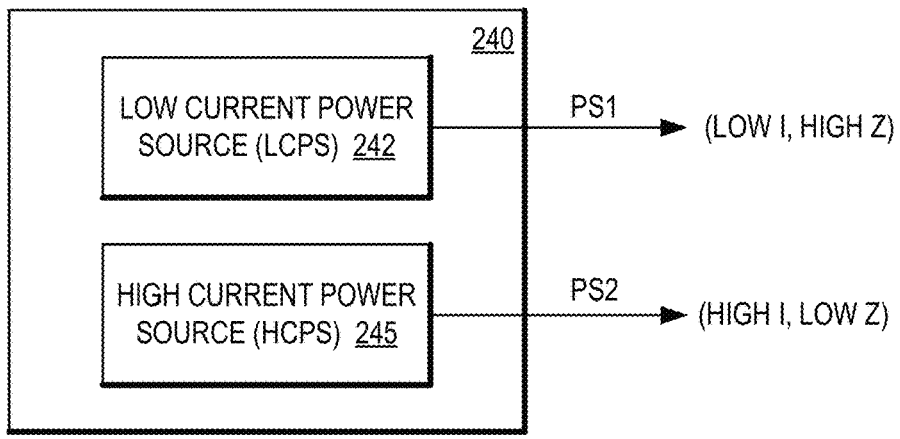
FIGS. 4A-4C are diagrams of a power supply of a WCD system in accordance with one or more embodiments.
Figure 4B:
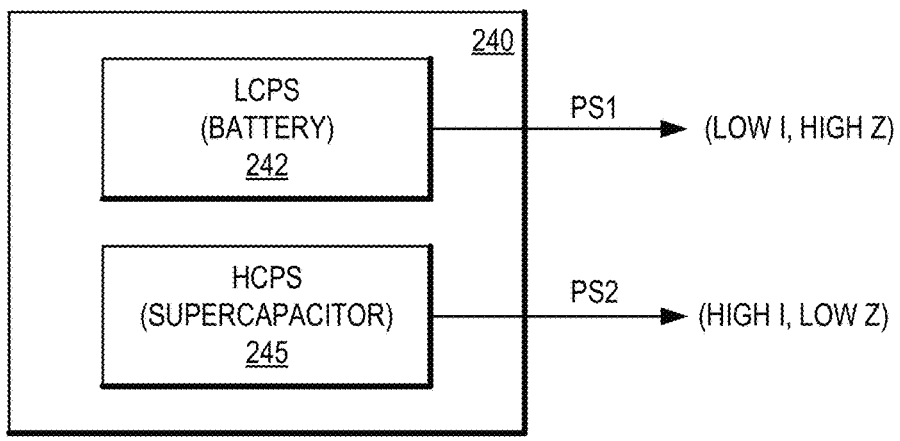
Figure 4C:
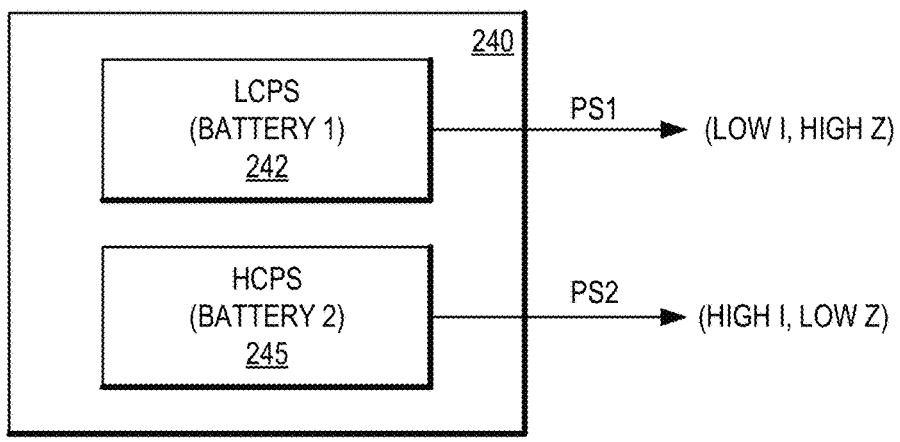

Referring now to FIGS. 4A-4C, diagrams of a power supply of a WCD system in accordance with one or more embodiments will be discussed. In FIG. 4A, a power supply 240 for a defibrillator 200 of a WCD system 10 can in general comprise a low current power source (LCPS) 242 to provide a first power supply PS1 for defibrillator 200, and a high current power source (HCPS) 245 to provide a second power source for defibrillator 200. The first power source PS1 can comprise a low current, high impedance (LOW I, HIGH Z) power source, and the second power source PS2 can comprise a high current, low impedance (HIGH I, LOW Z) power source.

In FIG. 4B, the LCPS 242 can comprise a battery (BATTERY), and the HCPS 245 can comprise a supercapacitor (SUPERCAPACITOR). In FIG. 4C, the LCPS 242 can comprise a first battery (BATTERY 1) and the HCPS 245 can comprise a second battery (BATTERY 2) that is a different type of battery than the first battery. In some embodiments, the HCPS 245 can be used to provide energy to power the HV capacitor charger 322 and/or other high current-draw loads of defibrillator 200 such as firing a squib or powering a fluid deployment mechanism as discussed in further detail herein below. The HCPS 245 can comprise a primary cell battery, a supercapacitor, or other power sources such as a secondary cell. The HCPS 245 can be optimized for high current draws, such those current draws that are intermittent. The LCPS 242 can be configured to power low current-draw loads such as lower power circuits and electronics of defibrillator 200. The LCPS 242 can comprise a secondary cell battery, a supercapacitor, or another power source. The LCPS 242 can be optimized for lower-power functionality, for example those that are more continuous such as the monitoring aspect and control circuitry of a wearable defibrillator. The monitoring circuitry 320 can include, for example, ECG sensing and data acquisition circuitry, a controller or processor for data analysis, or other defibrillator 200 support circuit functions.

In some embodiments such as shown in FIG. 4C, LCPS 242 can comprise a power source such as a low current battery (BATTERY 1), and HCPS 245 can comprise a relatively high current secondary cell battery or a primary cell battery (BATTERY 2), or a high current capacity energy storing source such as a super capacitor as shown in FIG. 4B. The LCPS 242 can be optimized to supply power to the patient monitoring circuitry 320 of defibrillator 200. In some embodiments, the HCPS 245 can comprise an inductor or in general any device capable of providing energy as a high current pulse, and the scope of the disclosed subject matter is not limited in these respects.

In some examples, for a given implementation of WCD system 10 with a single power source, a steady state power draw for monitoring/control circuitry 320 can be approximately 50 milliwatts (mW) with peaks of up to 500 mW, assuming the peaks occur approximately 5% of the time. In some examples, the power source can be a lithium-ion battery such as the PANASONIC NCA793540 battery which is a 1570 milliamp hour (mAh) battery with a rated discharge of up to 1.57 amperes (A). This battery would be sufficient to power the monitoring/control circuitry 320 for a day over a 24-hour period, and the energy draw would be 1.74 watt-hours (Wh) based on the calculation of 24 hours* (0.05 W*95%+0.5 W*5%, or 483 mAh based on a calculation of 1.74 Wh/3.6 volts (V), where 3.6 V is the nominal battery voltage. This battery, however, would be insufficient for charging the defibrillator capacitor 252. For a 170 joule (J) defibrillation shock, defibrillation capacitor 252 should be charged to 190 J in order to deliver the 170 J in about 12 seconds (s) at about 50% efficiency, and the power required would be about 31.7 W calculated as (190 J)/(50%)/(12 s). With a nominal voltage of 3.6 V, the above noted NCA battery cell can offer about 5.65 W. As a result, six cells would be required to offer a sufficient battery pack, for example three parallel paths of two series battery cells would be a 7.2V battery with a current discharge capability of 4.71 A. The cells have a volume of 11.3 cubic centimeters each, calculated as 7.95 millimeters (mm)*35.1 mm*24.7 mm, so the whole battery pack would occupy a total volume of 67.8 cubic centimeters in addition to control circuitry to configure a parallel battery arrangement.

In some embodiments, such as the example of FIG. 4B where the HCPS 245 comprises a super capacitor and the LCPS 242 comprises a battery, the following design can be realized. For illustrative purposes, steady state power draw for monitoring/control circuitry 320 can be approximately 50 mW with peaks of up to 500 mW where the same NCA793549 battery cell is used for the LCPS 242. For the HCPS 245, it can be assumed that it is intended to supply five defibrillation shocks in sequence for a given episode with no charging in between the five shocks. The energy to be stored in the supercapacitor of HCPS 245, assuming the same 190 J per defib shock and 50% charging efficiency, is 1900 J as calculated by (190 J/defib shock)*(5 defib shocks)/(50%). An example supercapacitor can be a VISHAY MAL219690108E3 which is a 90 farad (F) capacitor rated for 8.4 V. If the supercapacitor will be charged to 7.2V which is the nominal voltage of two battery cells, the energy stored in the supercapacitor is then 2333 J calculated as $(0.5)*(C)*(V^2)$, allowing for some buffer over the necessary 1900 J. This example supercapacitor comprises an elliptic cylinder of volume of about 13.7 cubic centimeters calculated from diameters of 25 mm and 35 mm and a height of 20 mm. If using the above-mentioned two NCA battery cells for the LCPS 242 and the above-mentioned MAL supercapacitor for the HCPS 245, the volume of two cells and the super capacitor totals approximately 36.3 cubic centimeters which is a volume savings of approximately 31 cubic centimeters over an embodiment comprising a total of six of the NCA battery cells. For the example discussed herein, assume the LCPS 242 needs to supply 3.5 V minimum and that the two serial cells can operate down to 6 V. The output current rating of LCPS 242 would need to be at least 0.5 A to sustain the peak functionality, and the output impedance could be at most 5 ohms as calculated by (6 V−3.5 V)/0.5 A. If it is assumed that the HCPS 245 needs 5 V minimum to function, the no-load voltage can be assumed to go as low as 6 V. The output current rating of HCPS 245 would need to be at least 4.4 A in this example, and the output impedance could be at most 0.23 ohms as calculated by (6 V−5 V)/4.4 A. It should be noted, however, that these are merely example values such that other output currents and output impedances can be provided for LCPS 242 and HCPS 245 depending on design requirements, and the scope of the disclosed subject matter is not limited in these respects.

In one or more embodiments, following a set of five defibrillation shocks delivered from defibrillation capacitor 252, the battery of LCPS 242 can be configured to charge the supercapacitor of HCPS 245 for future shocks. Alternatively, the batter of LCPS 242 can directly charge the defibrillation capacitor for future shocks. For the example, after delivery of five shocks from the defibrillation capacitor 252, the supercapacitor of HCPS 245 can have about 433 J left as calculated by 2333 J from a full charge less 1900 J consumed in charging the defibrillation capacitor 252, corresponding to about 3.1 V on the supercapacitor. Assuming a 1 A charging rate with 1.57 A current limit rating of the above example NCA battery cell, minus the 0.5 A peak current draw for the monitoring/control circuitry 320 approximately equals about 1 A. A supercapacitor such as the noted MAL219690108E3 supercapacitor has a recommended charge current of 0.3 A to 1 A, so the charge time or recharge time would be about 369 seconds as calculated from dt equals C*dV/I or (90 F)*(7.2 V−3.1 V)/1 A], or about 6.15 minutes to recharge the supercapacitor after delivering five shocks to be ready to charge the defibrillation capacitor 252 for the delivery of five additional shocks. It should be noted that the above values and ratings for a battery of LCPS 242 and supercapacitor of HCPS 245 are provided for purposes of discussion and example, and the scope of the disclosed subject matter is not limited in these respects. In the example discussed herein, a high-impedance would not interfere with a 0.5 A current draw, but possibly would interfere with a 4.4 A current draw, for example based on 31.7 W power draw divided by the nominal 7.2 V of the battery pack. In such an example as discussed above, the single cell which could run the LCPS 242 could be realized as a battery pack of six cells in order to generate a HCPS 245. In other examples, however, the context could change based on the design. For example, in another design, LCPS 242 may be required to support 4.4 A, and the HCPS may be required to support 20 A. It should be noted, however, that these are merely example design values, and the scope of the disclosed subject matter is not limited in these respects.

In general. the constraints around the HCPS 245 are defined by the particular design implementation. The peak current demand is defined by the system, namely whichever high-current-demand circuit has the greatest current demand, for example a defibrillation capacitor charger, fluid deployment mechanism, a gel deployment mechanism, a squib, a communication link, a positioning location system, and so on. In the case of the capacitor charger, power demand can be determined from the desired charge time and the energy needed on the defibrillation capacitor. The peak current can then be determined by the voltage of the HCPS 245 (P=I*V). For a minimum case, assume something on the order of a 100 microfarad (μF) capacitor charged to 1600 V in 12 seconds with a 50% efficient charger and a 10.8 V HCPS 245. The needed current would then be approximately 2 A. For a maximum case, assume a 360 μF capacitor charged to 5000 V in 6 s with a 50% efficient charger and a 6 V HCPS. The needed current would then be approximately 250 A.

The HCPS 245 impedance will then depend on the peak current and the minimum voltage to maintain the high-current-demand circuit's functionality (V_hcps−V_circuit)/I_peak). This resistance would necessarily include parasitic power-path impedance. Continuing from the minimum case, assuming 5 V would be needed to power the high-current-demand circuit, the impedance could be at most 2.9 ohms calculated as (10.8 V−5 V)/(2 A). Continuing from the maximum case, also assuming 5 V is needed for the high-current-demand circuit, the impedance would be at most 0.004 ohms calculated be (6 V−5 V)/(250 A).

The LCPS 242 constraints are also defined by the particular design implementation. The current demands are defined by the system needs and can vary depending on the structure of the controls and the number and/or types of peripherals. One low-end example could be a 100 mA load with a 3.6 V LCPS 242. Another high-end example could be a 10 A load with a 10.8 V LCPS 242. Assuming the circuitry driven by the LCPS needs a 3 V minimum, the maximum impedance of the low-end example would be 6 ohms as calculated by (3.6 V−3 V)/(0.1 A). The maximum impedance of the high-end example would be 0.78 ohms as calculated by (10.8 V−3 V)/(10 A).

In general, LCPS 242 can have an output current from about 0 A to about 10 A and an output impedance from about 0 ohms to about 6 ohms. In general, HCPS 245 can have an output current from about 2 A to about 250 A and output impedance from about 0 Ohms to about 2.9 ohms. It should be noted, however, that these are merely example values such that other output currents and output impedances can be provided for LCPS 242 and HCPS 245 depending on design requirements, and the scope of the disclosed subject matter is not limited in these respects. In general, the LCPS 242 impedance will be greater than the HCPS 245 impedance for a given design.

Figure 5A:
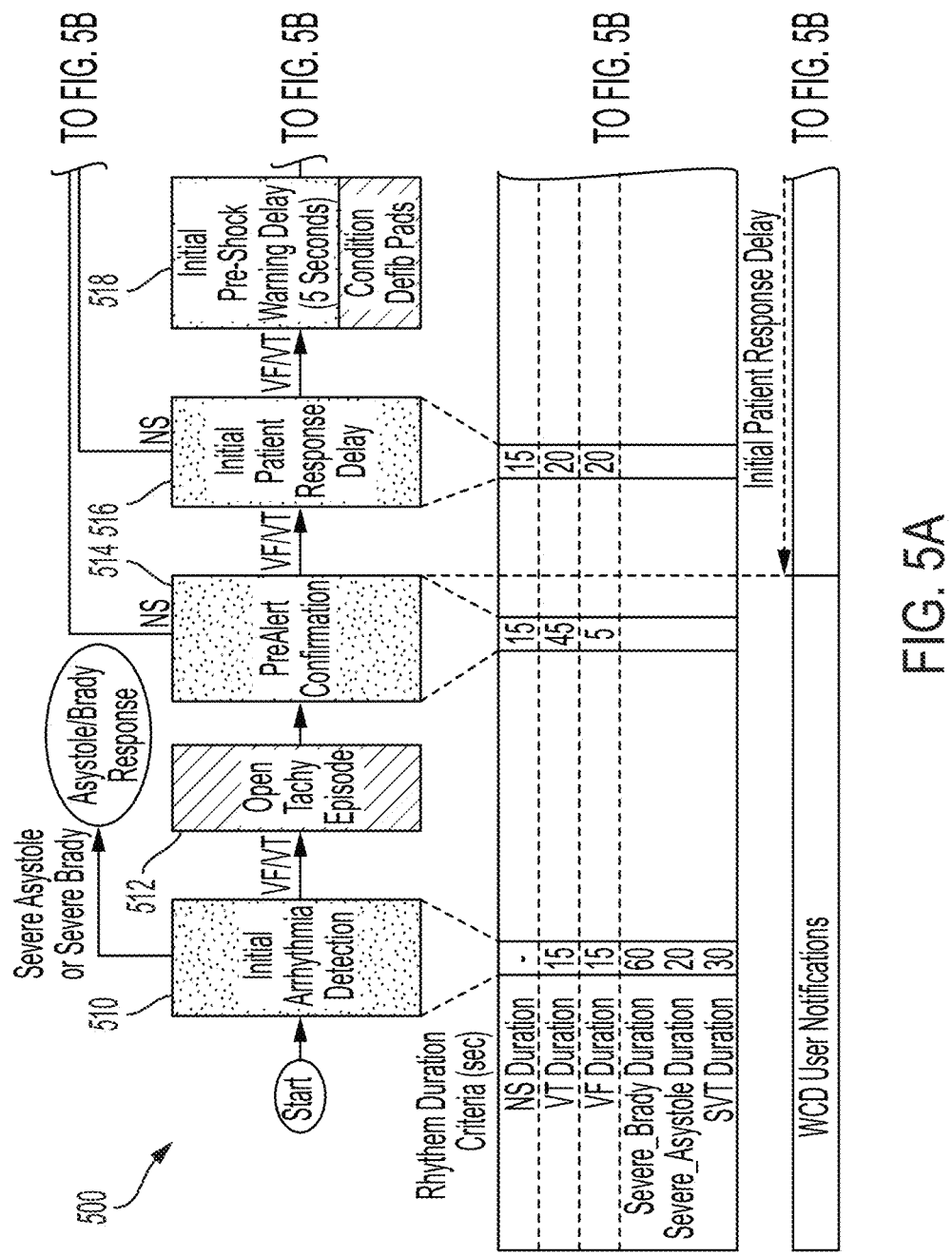
FIGS. 5A-5B are a diagram of a process to identify heart arrhythmias and to apply one or more shocks to a patient in accordance with one or more embodiments.
Figure 5B:
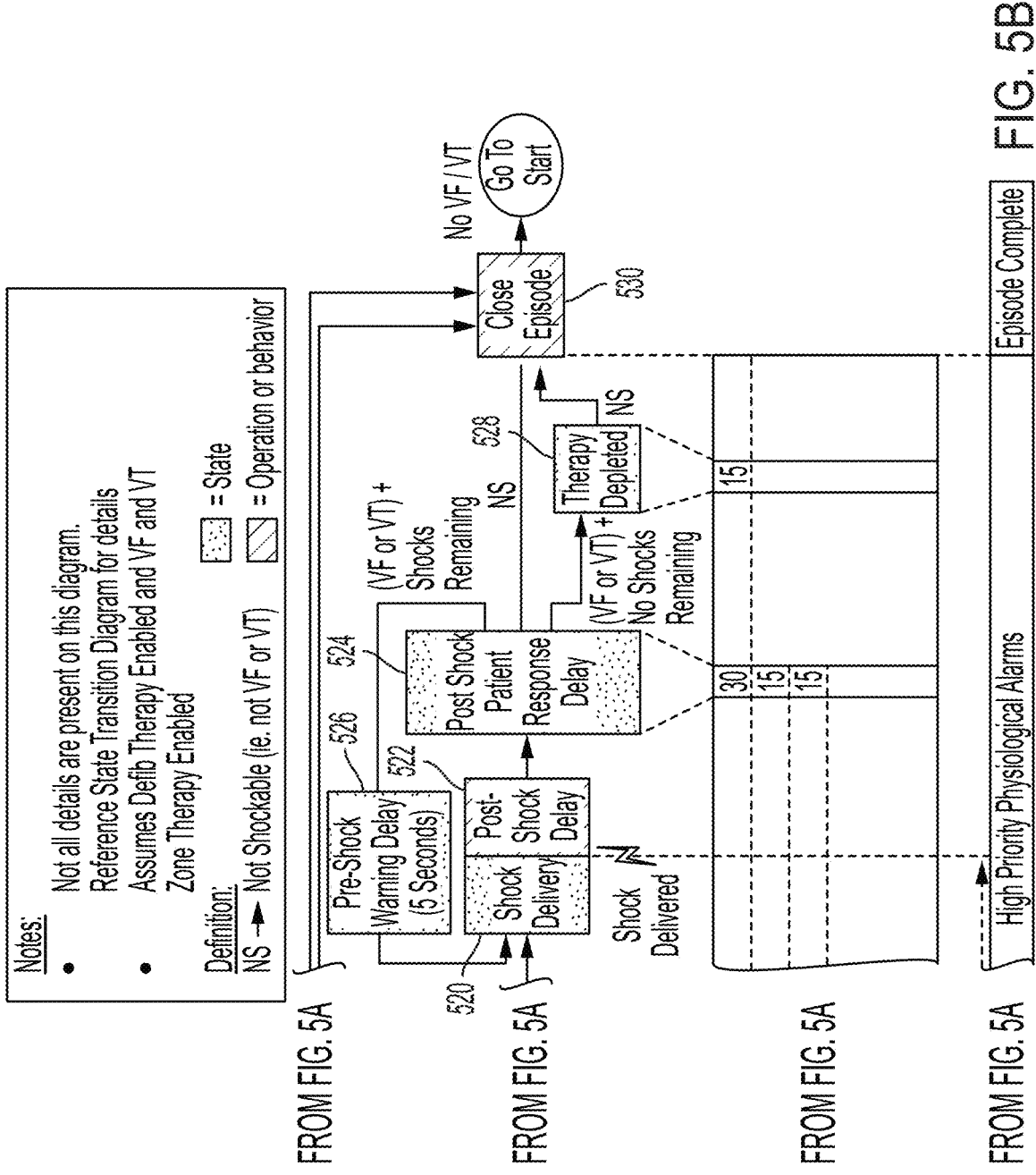

Referring now to FIGS. 5A-5B, a diagram of a process to identify heart arrhythmias and to apply one or more shocks to a patient in accordance with one or more embodiments will be discussed. The example process shown in FIG. 5A and FIG. 5B can incorporate LCPS 242 and HCPS 245 to charge the defibrillation capacitor 252 to provide one or more therapy shocks 111, and to execute one or more iterations of charging the defibrillation capacitor 252, providing one or more shocks 111, recharging the HCPS 245 with the LCPS 242, and providing one or more additional shocks 111 as incorporated in method 500. In method 500, arrhythmia detection starts with a 15 second initial arrhythmia detection period at block 510. If the rhythm is detected as being shockable for 15 seconds, then an episode is opened at block 512. After an episode is opened, there is a pre-alert confirmation period at block 514 before an alarm is given. In some embodiments, for ventricular fibrillation (VF) the confirmation period at block 514 is five seconds and for ventricular tachycardia (VT) the confirmation period at block 514 is 45 seconds. In other embodiments, different confirmation periods may be utilized.

The WCD system 10 alarms for a period of time referred to as the Initial Patient Response Delay at block 516. If the patient 82 or 282 does not respond, then a shock is given at block 520 after an Initial Pre-Shock Warning Delay at block 518 which may be, for example, five seconds. A Post Shock Delay at block 522 occurs after shock delivery, followed by a Post Shock Patient Response Delay at block 524. Depending on the state of VF or VT and whether there are shocks remaining to be delivered by WCD system 10, another shock delivery may occur at block 520 after Pre-Shock Warning Delay at block 526. For example, the energy to deliver one or more shocks can be stored in the HCPS 245 to charge the defibrillator capacitor 252, which can comprise one or multiple capacitors in some embodiments. The amount of energy stored in the HCPS 245 can be sufficient to deliver one or more shocks from the defibrillator capacitor 252 during a given episode until the energy stored in the defibrillation capacitor 252 is depleted. In some examples, defibrillation capacitor 252 can deliver up to five shocks during an episode after being charged by the HCPS 245. In general, after a first shock, if there is enough energy in the HCPS 245 and/or defibrillation capacitor 252, the defibrillator capacitor 136 can be recharged one or more times to deliver one or more additional shocks. In some embodiments, the defibrillator capacitor 252 is recharged after every shock, and it typically takes about six seconds to charge the defibrillator capacitor 252 for each shock. The only physical limit to the number of shocks during an episode that can be delivered is the energy in the HCPS 245. If the HCPS 245 has enough energy remaining to charge the defibrillator capacitor 252 one or more times, then WCD system 10 can be considered as having remaining shocks to be delivered during an episode.

Multiple shocks can be delivered during an episode until the WCD system 10 determines that an additional shock would not be effective. In some embodiments, the WCD system 10 stops delivering shocks after five shocks have been delivered. Delivery of multiple shocks can occur via a loop comprising block 520, block 522, block 524, and block 526. This loop can be repeated depending on the state of VF or VT and whether there are any remaining shocks to be delivered based on the amount of energy remaining in the HCPS 245 and defibrillation capacitor 252. If therapy is depleted at block 528, meaning there is not enough energy left in the HCPS 245 to deliver another shock, or if there is no longer VF or VT, the episode can be closed at block 530. After an episode, the HCPS 245 can be recharged by LCPS 242 to have sufficient energy to charge the defibrillation capacitor 252 for one or more subsequent episodes. This discharge and recharge process can be iterated one or more times, for up to five episodes in some embodiments, or until there is insufficient energy stored in LCPS 242, HCPS 245, and/or defibrillation capacitor 252. In one example, enough energy can be stored in LCPS 242 and HCPS 245 when fully charged to provide up to five episodes with up to five shocks 111 being delivered per episode for a total of 25 shocks 111, although this is merely one example of the number of shocks 111 that can be delivered by an example WCD system 10, and the scope of the disclosed subject matter is not limited in these respects. An example of such an iterative process is shown in and described with respect to FIG. 6 below.

Figure 6:
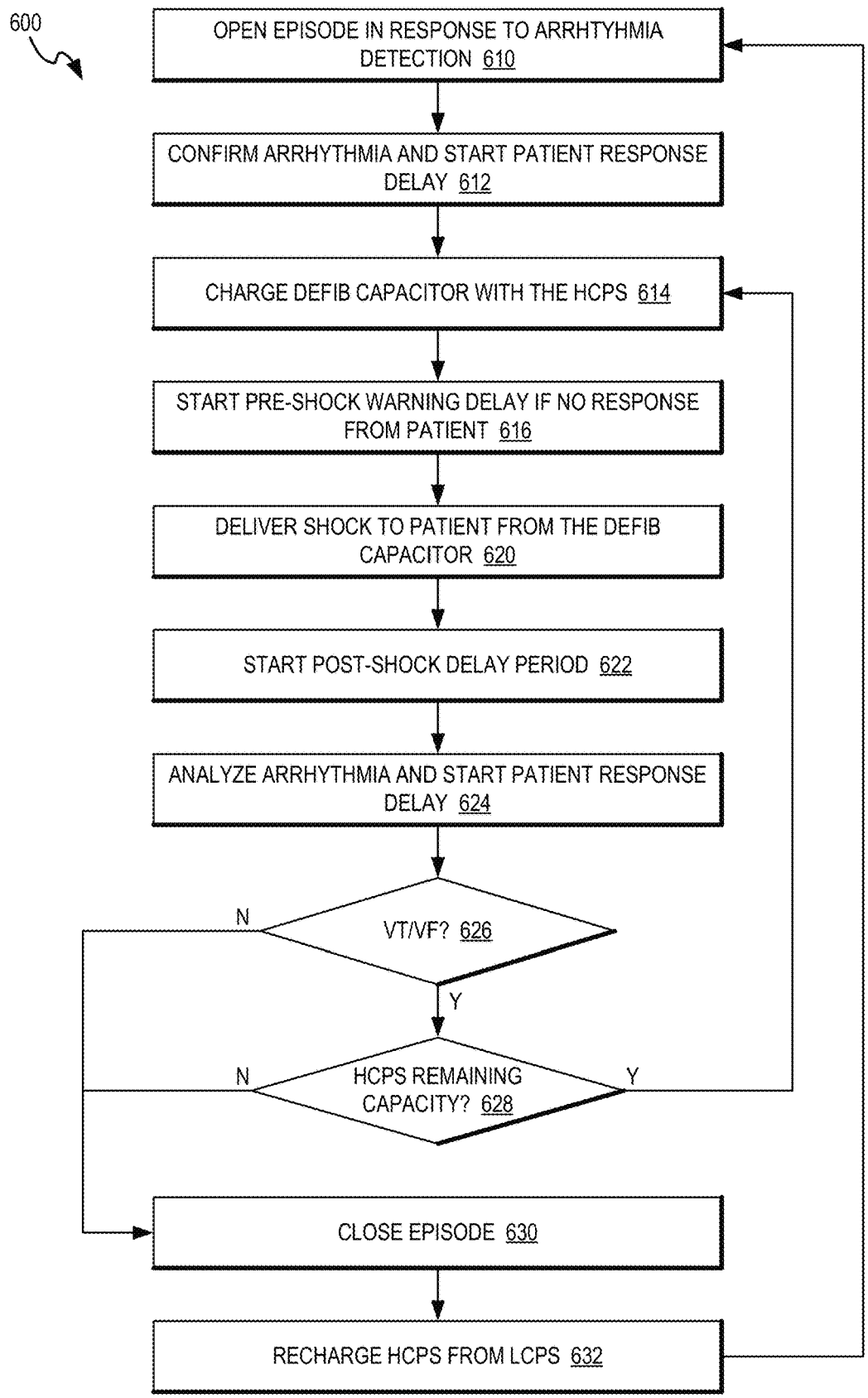
FIG. 6 is a flow diagram of a method to apply one or more shocks to a patient using the power components of FIG. 3 in accordance with one or more embodiments.

Referring now to FIG. 6, a flow diagram of a method to apply one or more shocks to a patient using the power components of FIG. 3 in accordance with one or more embodiments will be discussed. FIG. 6 shows one particular method 600 to incorporate charging of a defibrillation capacitor 252 from an HCPS 245 and recharging the HCPS 245 from LCPS 242. It should be noted that method 600 may include more operations or fewer operations, which may be in various other alternative orders, and the scope of the claimed subject matter is not limited in these respects. In some embodiments, method 600 may be executed by processor 230 of defibrillator 200 as shown in FIG. 2, or in general by monitoring circuitry 320 as shown in FIG. 3, and may be understood with respect to the process of FIG. 5A and FIG. 5B as one example.

At operation 610, an episode can be opened in response to detection of a possible arrhythmia in patient 82 or patient 282. Arrhythmia can be confirmed, and the patient response delay period can be started at operation 612. The defibrillation capacitor 252 can be charged with the HCPS 245 at operation 614. If no intervening response is received from the patient during the patient response delay period, the pre-shock warning delay period can start at operation 616, and an alarm can sound indicating that delivery of a shock is imminent. At operation 620, a shock can be delivered to the patient from the defibrillation capacitor 252, and then the post-shock delay period can be started at operation 622.

The arrhythmia can continue to be analyzed at operation 624, and the patient response delay period can be started. A determination can be made at decision block 626 whether patient is still experiencing shockable VT or VF. If the patient is no longer experiencing shockable VT or VF, then the episode can be closed at operation 630. Otherwise, if the patient is still experiencing shockable VT or VF, then a determination can be made at decision block 628 whether the HCPS 245 has any remaining capacity. If not, then the episode can be closed at operation 630. Otherwise, if the HCPS 245 has remaining capacity, the HCPS 245 can charge the defibrillation capacitor 252 at operation 614, and method 600 can continue to iterate to deliver additional shocks 111 until the patient is no longer experiencing shockable VT or VF, or until there is insufficient capacity in the HCPS 245 to charge the defibrillation capacitor, and the episode can be closed at operation 630. After the episode is closed, the HCPS 245 can be recharged from the LCPS 242, and method 600 can repeat starting at operation 610 for one or more additional episodes until there is insufficient energy remaining in the LCPS 242 to recharge the HCPS 245.

In accordance with one or more embodiments, the separation of the power supply 240 of defibrillator 200 as utilized in a WCD system 10 into low current power source (LCPS) 242 and a high current power source (HCPS) 245 allows the LCPS 242 to be optimized for delivery of power for devices and systems that have lower current, lower impedance source power requirements. Similarly, the HCPS 245 can be optimized to deliver power to devices and systems that have higher current, higher impedance source power requirements where energy is to be delivered as a large pulse of current. As discussed herein above, such a large pulse of current from the HCPS 245 can be used to charge the defibrillation capacitor 252 of the defibrillator 200. In another embodiment, the HCPS 245 can be used to provide a large pulse of current to a mechanism used to deploy a conductive fluid or gel to the interface between the defibrillation electrodes 104 and 108 of FIG. 1 or 204 and 208 of FIG. 2 and the patient's skin prior to providing one or more shocks to the patient. Such a deployment of conductive fluid or gel can be performed using a fluid deployment mechanism or squib for immediate or rapid dispensing of the fluid or gel, for example as discussed in published patent application Pub. No. US 2020/0121938 A1 which is hereby incorporated herein by reference in its entirety.

In another embodiment, the HCPS 245 can be used to provide or send an emergency alarm, signal, beacon, or transmission in response to detection of an arrhythmia in the patient 82 by the WCD system 10. In such embodiments, the patient 82 could be unconscious, and the HCPS 245 can be used to power such devices or transmissions on a short-term basis by being powered by the HCPS 245 for the duration of an episode, and/or for some period thereafter. For example, the HCPS 245 can power a satellite link and/or a Global Positioning System (GPS) device to obtain the location of the patient and to transmit the location, including for example GPS coordinates, to a remote user or facility. The HCPS 245 further can be used to power a modem or telephone device including a cellular telephone or modem to call emergency services such as 911 or other emergency services to allow for emergency medical technicians (EMTs) or other similar personnel to be directed to the patient 82 for further assistance. In some embodiments, the HCPS 245 can be used to transmit a locator beacon signal so that personnel with the appropriate beacon locator equipment can be directed to the location of the patient 82. It should be noted that these are merely examples of applications for the HCPS 245 as described herein, and the scope of the disclosed subject matter is not limited in these respects.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment, removing one or more features from an embodiment, or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the operations, acts, or modalities of a method.

Although the claimed subject matter has been described with a certain degree of particularity, it should be recognized that elements thereof can be altered by persons skilled in the art without departing from the spirit and/or scope of claimed subject matter. It is believed that the subject matter pertaining to power in a wearable cardioverter defibrillator (WCD) and many of its attendant utilities will be understood by the foregoing description, and it will be apparent that various changes can be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable medical device, comprising:
   monitoring circuitry to monitor one or more patient parameters of a patient;
   defibrillation circuitry to provide one or more defibrillation shocks to the patient responsive to a control signal from the monitoring circuitry, wherein the defibrillation circuitry comprises a defibrillation capacitor to provide energy for the one or more defibrillation shocks; and
   a power source to provide power to the monitoring circuitry and the defibrillation circuitry, wherein the power source comprises:
      a low current power source (LCPS) configured to store a first electrical charge and to provide power to the monitoring circuitry; and
      a high current power source (HCPS) configured to store a second electrical charge and to provide power to the defibrillation circuitry;
   wherein:
      the LCPS comprises a high impedance power source configured to provide a first output, and the HCPS comprises a low impedance power source configured to provide a second output that is separate from the first output;
      the first output is coupled to the monitoring circuitry and the second output is not coupled to the monitoring circuitry; and
      the second output is coupled to the defibrillation circuitry and the first output is not coupled to the defibrillation circuitry.

2. The wearable medical device of claim 1, wherein:
   the defibrillation circuitry has a higher current draw than the monitoring circuitry.

3. The wearable medical device of claim 1, wherein:
   the HCPS is configured to charge the defibrillation capacitor to a predetermined voltage within a predetermined time.

4. The wearable medical device of claim 1, wherein:
   the LCPS comprises a battery; and
   the HCPS comprises a supercapacitor.

5. The wearable medical device of claim 1, wherein:
   the LCPS comprises a first battery; and
   the HCPS comprises a second battery that is a different type of battery than the first battery.

6. The wearable medical device of claim 1, further comprising an HCPS charging circuit, wherein the LCPS is configured to top off the HCPS via the HCPS charging circuit to accommodate charge loss in the HCPS.

7. The wearable medical device of claim 1, further comprising:
an HCPS charging circuit;
wherein:
the HCPS charging circuit is configured to charge the defibrillation capacitor to provide energy to the defibrillation capacitor for the one or more defibrillation shocks; and
the LCPS is configured to recharge the HCPS via the HCPS charging circuit after the HCPS has charged the defibrillation capacitor.

8. The wearable medical device of claim 7, wherein:
the HCPS is configured to provide power to one or more high-current draw loads in addition to the defibrillation capacitor; and
the one or more high-current draw loads include a fluid deployment mechanism, a gel deployment mechanism, a squib, a communication link, or a positioning location system.

9. The wearable medical device of claim 1, wherein:
the HCPS is configured to provide power to the monitoring circuitry when charge in the LCPS is below a threshold level.

10. A wearable cardioverter defibrillator (WCD) system, comprising:
a support structure to be worn by a patient including a plurality of electrodes to contact the patient's skin;
monitoring circuitry comprising a processor to monitor an electrocardiogram (ECG) signal of the patient obtained via the plurality of electrodes;
defibrillation circuitry comprising a defibrillation capacitor to provide energy for one or more defibrillation shocks, wherein the defibrillation circuitry is configured to provide the one or more defibrillation shocks to the patient via two of the plurality of electrodes;
a low current power source (LCPS) configured to store a first electrical charge and to provide a low current, high impedance power output to power the monitoring circuitry; and
a high current power source (HCPS) configured to store a second electrical charge and to provide a high current, low impedance power output to the defibrillation circuitry;
wherein:
the LCPS is configured to provide a first output and the HCPS is configured to provide a second output that is separate from the first output;
the first output is coupled to the monitoring circuitry and the second output is not coupled to the monitoring circuitry; and
the second output is coupled to the defibrillation circuitry and the first output is not coupled to the defibrillation circuitry; and
wherein the processor is configured to:
determine whether a shockable event has occurred in the patient based at least in part in the ECG signal; and
send a control signal to the defibrillation circuitry to cause the HCPS to charge the defibrillation capacitor in response to the shockable event.

11. The WCD system of claim 10, wherein:
the LCPS comprises a battery; and
the HCPS comprises a supercapacitor.

12. The WCD system of claim 10, wherein:
the LCPS comprises a first battery; and
the HCPS comprises a second battery that is a different type of battery than the first battery.

13. The WCD system of claim 10, wherein:
the LCPS and the HCPS are contained within a same housing, wherein the housing comprises a removable pack.

14. The WCD system of claim 10, wherein:
the LCPS is contained within a housing that comprises a removable pack that does not contain the HCPS.

15. The WCD system of claim 10, further comprising:
a first charger circuit configured to charge the LCPS; and
a second charger circuit configured to charge the HCPS.

16. The WCD system of claim 10, wherein:
the LCPS is configured to recharge the HCPS via an HCPS charging circuit after the HCPS charges the defibrillation capacitor.

17. The WCD system of claim 10, wherein:
the LCPS is configured to provide a maintenance charge to the HCPS via an HCPS charging circuit to offset charge loss in the HCPS.

18. The WCD system of claim 10, wherein:
the HCPS is configured to provide power to one or more high-current draw loads in addition to the defibrillation circuitry; and
the one or more high-current draw loads include a fluid deployment mechanism, a gel deployment mechanism, a squib, a communication link, or a positioning location system.

19. The WCD system of claim 10, wherein:
the HCPS is configured to charge the defibrillation capacitor to a capacity sufficient to provide a plurality of shocks to the patient from a single charge from the HCPS.

* * * * *